United States Patent
Ishida

(10) Patent No.: US 8,367,622 B2
(45) Date of Patent: Feb. 5, 2013

(54) SULFATED C-GLYCOSIDE, METHOD FOR ISOLATING SAME AND METHOD FOR SYNTHESIZING SAME

(75) Inventor: Hitoshi Ishida, Shizuoka (JP)

(73) Assignee: Shizuoka Prefecture Public University Corporation, Shizuoka (JP)

( * ) Notice: Subject to any disclaimer, the term of this patent is extended or adjusted under 35 U.S.C. 154(b) by 0 days.

(21) Appl. No.: 13/143,111

(22) PCT Filed: Dec. 25, 2009

(86) PCT No.: PCT/JP2009/071700
§ 371 (c)(1),
(2), (4) Date: Sep. 26, 2011

(87) PCT Pub. No.: WO2010/076879
PCT Pub. Date: Jul. 8, 2010

(65) Prior Publication Data
US 2012/0029183 A1 Feb. 2, 2012

(30) Foreign Application Priority Data
Jan. 3, 2009 (JP) ................. 2009-000008

(51) Int. Cl.
| | | |
|---|---|---|
| A01N 43/04 | (2006.01) | |
| A61K 31/70 | (2006.01) | |
| C07H 5/02 | (2006.01) | |
| C07H 1/00 | (2006.01) | |
| C07H 1/06 | (2006.01) | |
| C07H 1/08 | (2006.01) | |

(52) U.S. Cl. ........... 514/23; 536/122; 536/124; 536/128

(58) Field of Classification Search .................. None
See application file for complete search history.

(56) References Cited

U.S. PATENT DOCUMENTS 5,296,469 A * 3/1994 Orjales-Venero et al. ...... 514/27

* cited by examiner

Primary Examiner — Traviss C McIntosh, III
(74) Attorney, Agent, or Firm — Wenderoth, Lind & Ponack, L.L.P.

(57) ABSTRACT

Provided are a sulfated C-glycoside which is a novel compound serving as a precursor of chafuroside and chafuroside analogs; a method for efficiently producing the sulfated C-glycoside; and a method for efficiently producing chafuroside and chafuroside analogs using said sulfated C-glycoside. A sulfated C-glycoside represented by general formula (A1) or (B1) [wherein $R_1$, $R_2$ and $R_3$ independently represent each a hydrogen atom or an OH group] is obtained by extracting tea leaves or tea tannins with water, a lower alcohol solvent having 1 to 3 carbon atoms or a liquid mixture comprising the same. Alternatively, the sulfated C-glycoside is produced by reacting a flavone C-glycoside such as isovitexin or vitexin with a sulfate group-introducing agent to thereby sulfate the flavone C-glycoside. By heating the sulfated C-glycoside thus obtained, chafuroside and chafuroside analogs are efficiently produced.

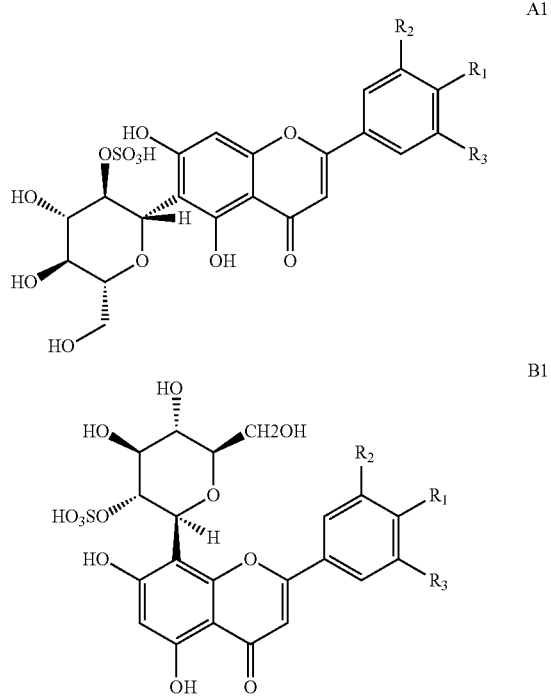

7 Claims, 1 Drawing Sheet

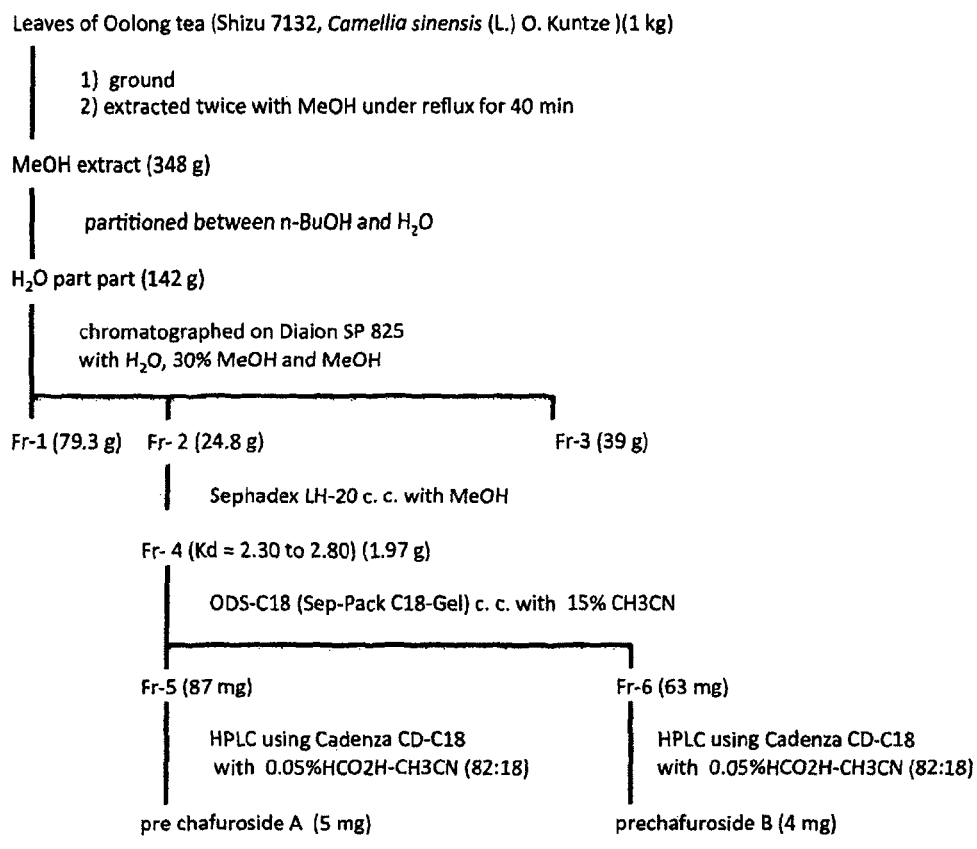

SULFATED C-GLYCOSIDE, METHOD FOR ISOLATING SAME AND METHOD FOR SYNTHESIZING SAME

TECHNICAL FIELD

The present invention relates to sulfated C-glycosides which are novel compounds. In more detail, the present invention relates to sulfated C-glycosides which are precursors of chafuroside and chafuroside analogs for which biological activities such as equal or higher anti-inflammatory effect compared with steroid or the like are expected; a method for isolating the same from tea leaves; a novel method for synthesizing the same; and a method for producing chafuroside and chafuroside analogs from said sulfated C-glycosides.

BACKGROUND ART

Chafuroside is a flavone C-glycoside which is one of flavone derivatives, and is known to exhibit properties such as antioxidant, antiallergic, anti-inflammatory and carcinogenesis inhibiting activities. It is known that chafuroside is a compound isolated from oolong tea, and its structural formula has been determined.

Uehara et al. carried out a test wherein atopic patients drunk every half amount of 400 ml of a thick solution condensed twice of commercially available oolong tea after breakfast and supper everyday for 4 weeks, and it was investigated whether daily dermal inflammation and intense itching accompanied thereby which were inherent to the patients could be prevented effectively or not, and had found that said oolong tea was effective in 62% of atopic patients who participated in this test (see Non-patent Document 1).

On the basis of the above-mentioned knowledge, Kasuya et al. tried to isolate effective ingredients from said oolong tea by using an effectiveness for an atopic disease model induced by 2,4-dinitro-fluorobenzene as an index for isolation. As a result, approximately 1 mg each of two ingredients exhibiting activities via oral administration was obtained from approximately 3.5 kg of tea leaves of the oolong tea, and structural formulas thereof were determined. Since they were novel compounds, they were given a name as "chafuroside A" and "chafuroside B" respectively (see Patent Document 1).

According to the above document, chafurosides A and B can be represented by the following formulas as A2-2 and B2-2 respectively:

[Chemical Formula 1]

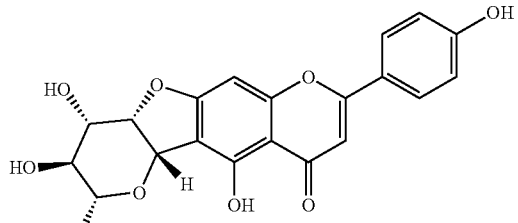

Chafuroside A (A2-2)

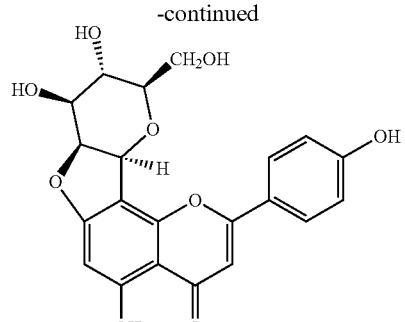

Chafuroside B (B2-2)

Subsequently, detailed studies were made on biological activities of chafurosides A and B. It was shown that, in an atopic disease model induced by 2,4-dinitro-fluorobenzene, chafuroside A exhibited a significant dermal inflammation-inhibiting activity at 10 µg/kg, which was comparable with a commercially available steroid anti-inflammatory agents "Prednisolone" (10 mg/kg) and "Betamethasone" (0.8 mg/kg) at a lower dosage (see Patent Document 1 and Patent Document 2).

In addition, it was confirmed that chafuroside A exhibited an effectively-inhibiting activity at 2.5 mg/kg which was a same dosage as indomethacin against intestinal polyp formation induced by azoxymethane (AOM) in a rat large bowel of a Min mouse. And it was assumed that this effect was caused by inhibitory action of chafuroside A to COX-2. In view of these results and the structure thereof, chafuroside A has a high probability of becoming a new type of anti-inflammatory agents (see Patent Document 2, Non-patent Document 3).

As mentioned above, chafurosides A and B exhibit more excellent biological activities than a steroid anti-inflammatory agent which is one of the most useful medicines at present and its usefulness is expected, and so, various methods for industrially producing them had been studied in the past.

For example, it was made an attempt to synthesize them from well-known flavone C-glycosides "isovitexin" and "vitexin" respectively. Among them, synthesis of chafurosides A and B from isovitexin and vitexin using Mitsunobu reaction represented by the following chemical reaction formula was proposed (Patent Document 2). However, since an azo reagent having high risk of explosion is used in this method, its industrialization is extremely difficult.

[Chemical Formula 2]

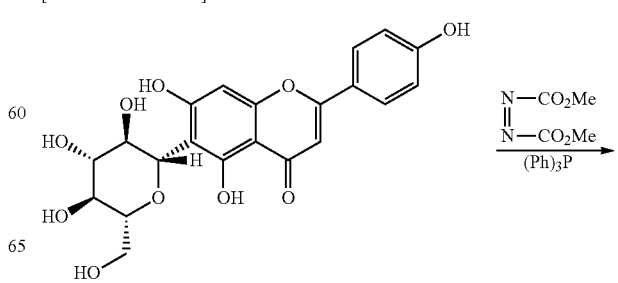

-continued

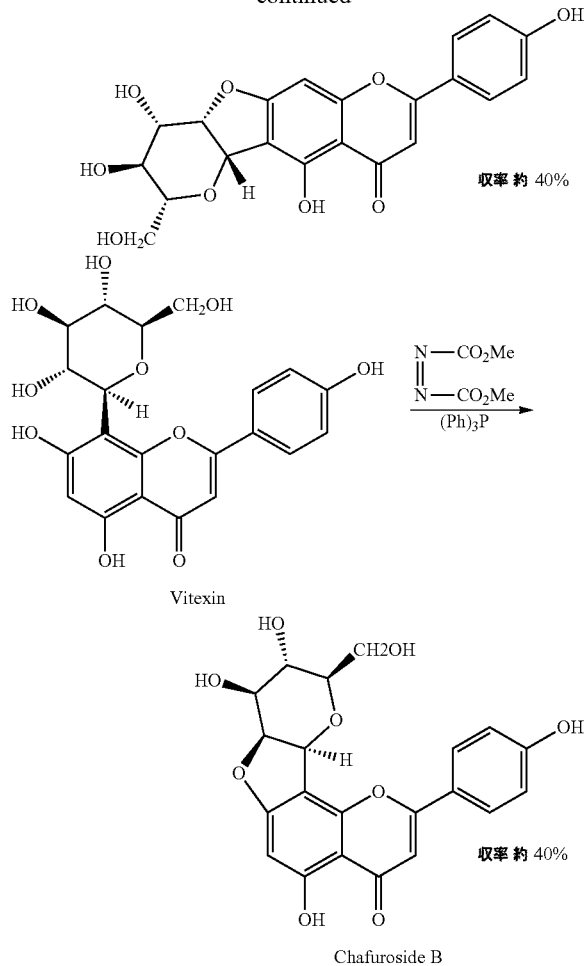

Vitexin

Chafuroside B

Although a novel chemical synthesizing method of chafuroside A is also disclosed in the above-mentioned Non-patent Document 2, the method has a defect of poor safety (see Patent Document 3, Patent document 4 and Non-patent Document 2).

In view of the structures, producing methods and biological activities of chafurosides A and B as mentioned above, production mechanism of chafurosides A and B in oolong tea leaves is very interesting. However, an industrial production method thereof which is simple in good yield, safe and inexpensive has not been established. In view of high usefulness of these compounds, it is strongly desired to develop an effective production method thereof.

PRIOR ART

Patent Document

[Patent Document 1] Jpn. Pat. Laid-Open Publication No. 2004-035474
[Patent Document 2] Jpn. Pat. Laid-Open Publication No. 2006-342103
[Patent Document 3] Jpn. Pat. Laid-Open Publication No. 2005-314260
[Patent Document 4] Jpn. Pat. Laid-Open Publication No. 2005-289888

Non-Patent Document

[Non-patent Document 1] Uehara et al., Dermatology Annals 92, 143-148 (1997)
[Non-patent Document 2] T. Nakatsuka et al., Bioorganic & Medicinal Chemistry Letters 14 (2004) 3201-3203
[Non-patent Document 3] N. Niho et al., Cancer Science 97 (2006) 248-251

DISCLOSURE OF THE INVENTION

Problems to be Solved by the Invention

The problem to be solved by the present invention is to provide a sulfated C-glycoside which is a novel compound as a precursor of chafuroside and chafuroside analogs, a method for efficiently producing the sulfated C-glycoside, and a method for efficiently producing chafuroside and chafuroside analogs using the same.

Means for Solving the Problems

The inventor carried out a study on the factors for producing chafurosides A and B, and succeeded in identifying said producing factors. On the basis of the result, the inventor isolated precursors of chafurosides A and B respectively, estimated the structure of each precursor as a novel compound by various physical-chemical data, and then made a structural determination by synthesis.

Furthermore, the inventor have found that, by heat-treatment, these precursors can be converted into chafurosides A and B respectively easily in good yield, that is, chafurosides A and B can be obtained from these precursors effectively in the extreme.

In addition, since it can be considered that, as represented by the general formula below, a compound having a partial structure (a) of the precursors of chafurosides A and B (the left side of the formula below) is converted into a compound having a partial structure (b) which is same as chafurosides A and B respectively (the right side of the formula below), it can be estimated that, from other groups of compounds having said partial structure (a), a group of compounds having same partial structure as chafurosides A and B would also be obtained similarly.

[Chemical Formula 3]

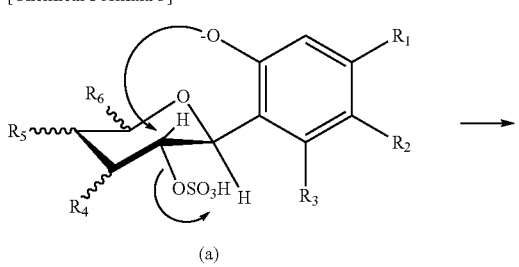

(a)

-continued

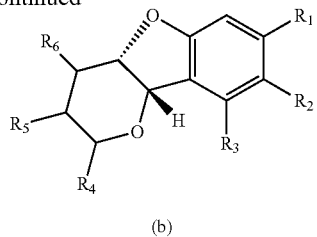

(b)

The inventor have found that, on the premise of the fact mentioned above, chafuroside and its analog compounds can be derived from 2-sulfate of sugar derivatives which can be acquired from nature or can be produced synthetically, and thus completed the present invention.

That is, the present invention provides a sulfated C-glycoside represented below, a method for isolating the same and synthesizing the same, and a method for producing chafuroside and its analogs from said sulfated C-glycoside.

(1) A sulfated C-glycoside represented by the following general formula (A1) or (B1):

[Chemical Formula 4]

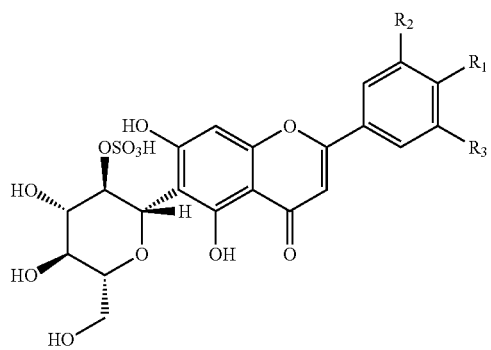

A1

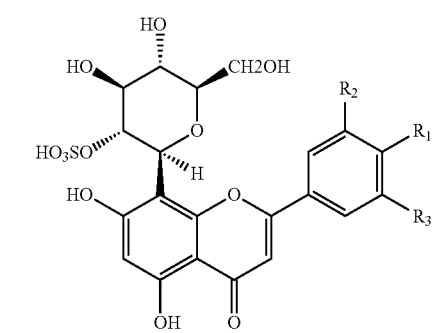

B1

(in the above general formula (A1) and (B1), each of $R_1$, $R_2$ and $R_3$ independently represents a hydrogen atom or an OH group.)

(2) The sulfated C-glycoside according to (1), wherein said sulfated C-glycoside is a sulfated derivative of isovitexin represented by the following formula (A1-2) or a sulfated derivative of vitexin represented by the following formula (B1-2).

[Chemical Formula 5]

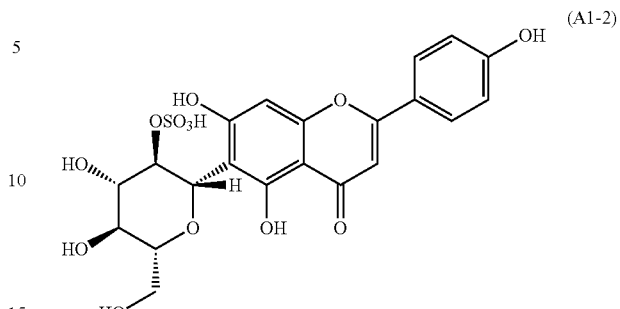

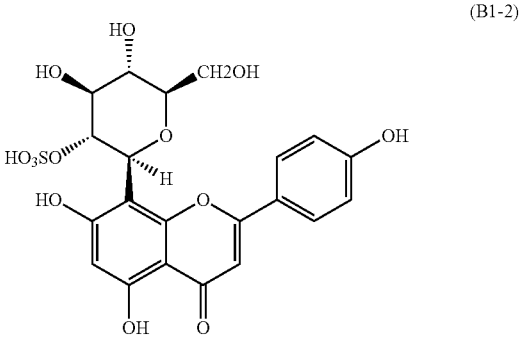

(3) A method for isolating a sulfated C-glycoside according to (1) or (2), which comprises a step of extracting said sulfated C-glycoside from tea leaves or tea tannins containing said sulfated C-glycoside using water, a lower alcohol solvent having 1 to 3 carbon atoms or a liquid mixture comprising the same.

(4) The method for isolating a sulfated C-glycoside according to (3), wherein the method comprises the following steps (IE), (RO) and (HA).

(IE) an extraction step wherein a ground product of tea leaves or tea tannins containing said sulfated C-glycoside is extracted with water, a lower alcohol solvent having 1 to 3 carbon atoms or a liquid mixture comprising the same to obtain an extraction liquid containing said sulfated C-glycoside, (RO) a concentration and dry-solidification step wherein said extraction liquid obtained by the above extraction step (IE) is concentrated, dried and solidified by heating under reduced pressure to obtain a dry solid substance containing said sulfated C-glycoside.

(HA) a purification step wherein said dry solid substance containing sulfated C-glycoside obtained by the above concentration and dry-solidification step (RO) is subjected to liquid-liquid partition using water and n-butanol solvent, and then the aqueous fraction is purified by a chemical separation purification method.

(5) A method for synthesizing sulfated C-glycoside according to (1) or (2), which comprises a step of reacting flavone C-glycoside represented by the following general formulas (A0) or (B0) with a sulfate group-introducing agent to sulfate said flavone C-glycoside.

[Chemical Formula 6]

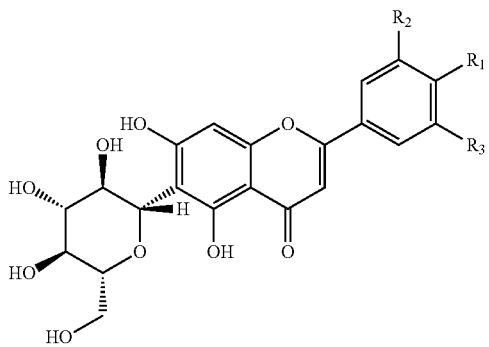

A0

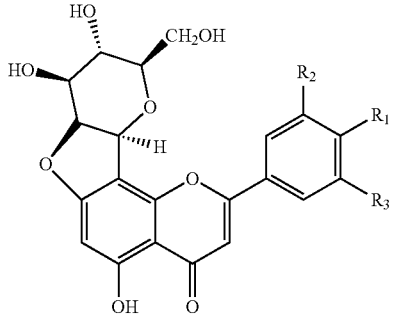

B2

(in the above general formula (A2) and (B2), each of $R_1$, $R_2$ and $R_3$ independently represents a hydrogen atom or an OH group.)

Effects of the Invention

According to the present invention, novel compounds of sulfated C-glycosides (sulfated derivatives of isovitexin and vitexin) as precursors of chafurosides A and B were isolated. Since the both compounds are novel compounds, the structures of them were estimated by various physical-chemical data and were determined by synthesis.

By the above results, it became clear that chafurosides A and B were produced from sulfated derivatives of isovitexin and vitexin respectively in tea leaves. To the inventor's knowledge, sulfated derivatives of flavone glycosides and flavone C-glycosides had not been found, and the inventor found these compounds for the first time in the present invention.

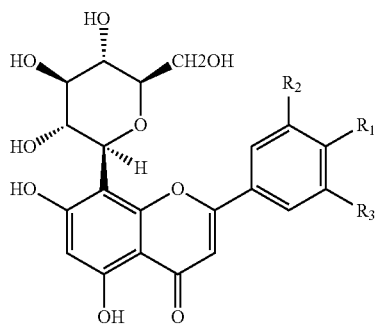

B0

(in the above general formula (A0) and (B0), each of $R_1$, $R_2$ and $R_3$ independently represents a hydrogen atom or an OH group.)

(6) The method for synthesizing sulfated C-glycoside according to (5), wherein said sulfate group-introducing agent is selected from the group consisting of pyridine-$SO_3$ complex, sulfur-DCC and triethylamine-$SO_3$ complex.

(7) A method for producing chafuroside and chafuroside analogs represented by the following formulas (A2) or (B2), which comprises a step of heating sulfated C-glycoside according to (1) or (2) at the temperature of 130-190° C.

Chafuroside A and Chafuroside B are produced from precursors of chafurosides A and B respectively by heating. It is reported that chafuroside A and chafuroside B exhibit anti-inflammatory effect, and especially, the effect of the former is more excellent than commercially available steroid agents.

According to the present invention, it is only confirmed that chafuroside A and chafuroside B are produced by the precursor of chafuroside A (isovitexin 2-sulfate) and the precursor of chafuroside B (vitexin 2-sulfate) respectively. However, it can be presumed that a compound having a same partial structure as the both precursors of chafuroside A and B can be converted into a compound having a same partial structure as chafuroside A and B respectively. It can be expected that the group of these compounds having the same partial structure as chafuroside A and B also exhibit excellent anti-inflammatory bioactivities like steroid.

Discovery of sulfated C-glycosides which are novel compounds as precursors of chafuroside and chafuroside analogs according to the present invention enables to search tea species or other food materials rich in chafuroside, to control the content of chafuroside in the process of producing food items from various types of tea leaves and other food materials and to produce tea and other food items rich in chafuroside, and therefore, its significance is great.

Sulfated C-glycosides of the present invention easily develop a cyclization reaction accompanied by steric inversion by heating in a solid state. Thus, a method for synthesizing chafuroside and chafuroside analogs at a low price which enables to synthesize chafuroside and chafuroside analogs from flavone C-glycoside such as isovitexin and vitexin through sulfate C-glycoside can be provided by the present invention. According to the present invention, since chafuro-

[Chemical Formula 7]

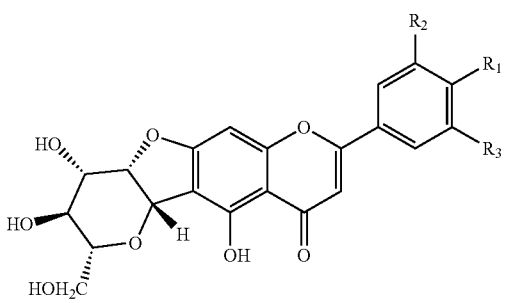

A2 side and chafuroside analogs can be produced in good yield using inexpensive and safe starting materials and reagents under relatively moderate reaction conditions, industrial mass production is feasible by a scale-up, and it is greatly useful on industry.

Considering the fact that sulfation has been correlated with mechanism of detoxification elimination in metabolism, the presence of precursors of chafuroside which are sulfated derivatives in tea leaves has great significance. As for isovitexin and vitexin, their anticancer effect, effect of reducing damages by UV irradiation, inhibiting effect of COX, antioxidant effect, antianxiety effect and the like have been drawing the attention recently. Since the precursors of chafurosides of the present invention which are novel compounds are sulfated derivatives and are easily soluble in water, transitivity to a human body thereof would be higher than isovitexin and vitexin which are very poorly soluble in water, and similar pharmacological effects as in isovitexin and vitexin regarding in vivo kinetics and biological activities will be expected.

There is a high possibility of being used as a novel type of naturally-derived anti-inflammatory agents having excellent safety in a higher yield.

Moreover, since the content of chafuroside precursor is small in a number of commercially available black tea, it would be interesting how the metabolic conversion would be occurred to the chafuroside precursor by oxidative enzyme reaction on fermentation during the production of tea.

BRIEF DESCRIPTION OF THE DRAWINGS

FIG. 1 shows a chart representing one example of a separating step of chafuroside precursor.

EMBODIMENT OF THE INVENTION

Embodiment of the present invention is described below.

(1) Sulfated C-Glycoside

Sulfated C-glycoside of the present invention is a novel compound which is a sulfated derivative of a flavone C-glycoside having a flavone skeleton represented by the following general formula (A1) or (B1).

[Chemical Formula 8]

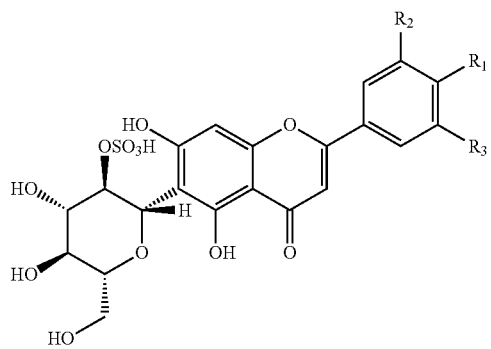

A1

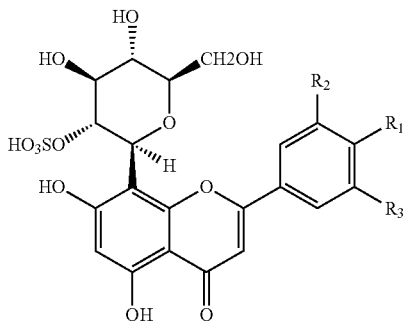

B1

In the above general formula (A1) and (B1), each of $R_1$, $R_2$ and $R_3$ independently represents a hydrogen atom or an OH group. Preferably, $R_1$ represents an OH group, and $R_2$ and $R_3$ represent a hydrogen atom respectively.

Examples of the compounds represented by the above general formula (A1) or (B1) include compounds A1-1, A1-2, A1-3, A1-4, B1-1, B1-2, B1-3 and B1-4 represented by the following formulas, wherein $R_1$, $R_2$ and $R_3$ represent synonymously with those in the above general formula (A1) and (B1) respectively.

[Chemical Formula 9]

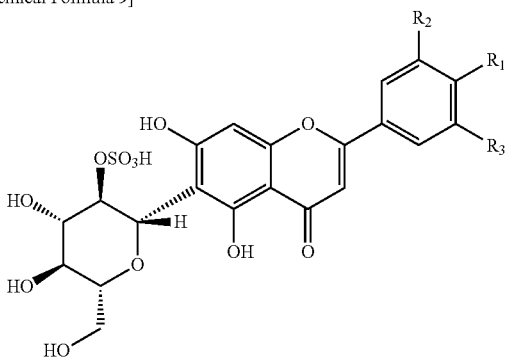

A1

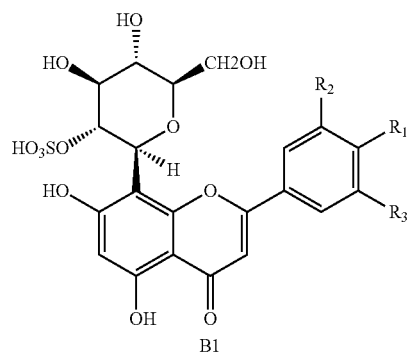

B1

| $R_1$ | $R_2$ | $R_3$ | |
|---|---|---|---|
| H | H | H | A1-1 |
| OH | H | H | A1-2 |
| OH | OH | H | A1-3 |
| OH | OH | OH | A1-4 |
| H | H | H | B1-1 |
| OH | H | H | B1-2 |
| OH | OH | H | B1-3 |
| OH | OH | OH | B1-4 |

Particularly preferable examples of the compounds represented by the above general formula (A1) include the chafuroside precursor A (or "prechafuroside A") which is the above compound (A1-2). This compound is a sulfated derivative of isovitexin (isovitexin 2"-sulfate).

Particularly preferable examples of the compounds represented by the above general formula (B1) include the chafuroside precursor B (or "prechafuroside B") which is the above compound (B1-2). This compound is a sulfated derivative of vitexin (vitexin 2"-sulfate).

(2) Method for Isolating Sulfated C-Glycoside in Tea Leaves

The sulfate C-glycoside represented by the above general formula (A1) or (B1) of the present invention can be isolated by extracting from tea leaves or tea tannins containing sulfate C-glycoside using water, a lower alcohol solvent or a liquid mixture thereof. That is, the method for isolating a sulfated C-glycoside according to the present invention is characterized in that it comprises a step of extracting said sulfated C-glycoside from tea leaves or tea tannins containing said sulfated C-glycoside using water, a lower alcohol solvent having 1 to 3 carbon atoms or a liquid mixture comprising the same.

Although specific processes for isolating should not be limited particularly, it is preferable that isolating is carried out by a method comprising the following steps (IE) to (HA):

(IE) an extraction step wherein a ground product of tea leaves or tea tannins containing said sulfated C-glycoside is extracted with water, a lower alcohol solvent having 1 to 3 carbon atoms or a liquid mixture comprising the same to obtain an extraction liquid containing said sulfated C-glycoside, (RO) a concentration and dry-solidification step wherein said extraction liquid obtained by the above extraction step (IE) is concentrated, dried and solidified by heating under reduced pressure to obtain a dry solid substance containing said sulfated C-glycoside, and (HA) a purification step wherein said dry solid substance containing sulfated C-glycoside obtained by the above concentration and dry-solidification step (RO) is subjected to liquid-liquid partition using water and n-butanol solvent, and then the aqueous fraction is purified by a chemical separation purification method.

In connection with the ground product of tea leaves or tea tannins containing sulfated C-glycoside used in the above extraction step (IE), examples of tea leaves include fresh tea leaves, tea leaves for green tea, tea leaves for houji tea, tea leaves for black tea and tea leaves for oolong tea. Particularly preferable examples include fresh tea leaves, tea leaves for green tea which is not strongly heated and oolong tea leaves. With regard to tea tannins containing sulfated C-glycoside, broken tea or a solid substance thereof which can be obtained mainly from a relatively brittle portion such as buds of tea leaves in the process of producing green tea can be used as bitter tea for tea tannins. Methods for grinding these tea leaves or tea tannins should not particularly be limited.

Examples of the lower alcohol solvents having 1 to 3 carbon atoms used in the above extraction step (IE) include methanol, ethanol and propanol. Preferable examples thereof include methanol. When extraction is carried out using water and methanol, more specifically, tea leaves or tea tannins containing sulfated C-glycoside is ground and is dispersed in water, and subsequently the ground product of tea leaves or tannins is extracted for 5-30 minutes at 5-70° C. using a methanol aqueous solution of 40-60 wt %, preferably 45-55 wt %, which is 5-20 times by volume, preferably 5-15 times by volume of said water to obtain an extraction liquid containing sulfated C-glycoside.

In the concentration and dry-solidification step (RO), it is particularly preferable that the extraction liquid obtained by the above extraction step (IE) is concentrated by heating up to a sufficient temperature (preferably to a temperature higher by 20° C. or more than the boiling point of the extraction liquid) under reduced pressure (preferably under reduced pressure of 10-500 mmHg) to evaporate the solvent of the extraction liquid, then heating is continued at the concentration temperature to remove the solvent substantially, and subsequently the substance dissolved in the extraction liquid is dried and solidified to obtain a dry solid substance containing sulfated C-glycoside.

In the above purification step (HA), the dry solid substance obtained containing sulfated C-glycoside obtained by the above concentration and dry-solidification step (RO) is subjected to liquid-liquid partition using water and n-butanol solvent, and then the aqueous fraction is purified by a chemical separation purification method. Examples of the chemical separation purification method include thin-layer chromatography, adsorption chromatography, partition chromatography, gel filtration chromatography, ion exchange chromatography, high-performance liquid chromatography (HPLC) and electrophoresis.

Unlike isovitexin and vitexin, the sulfated C-glycoside is a highly polar substance which has high water solubility caused by the presence of a sulfate group. Therefore, the sulfated C-glycoside is comprised in the aqueous fraction after liquid-liquid distribution, whereas isovitexin, vitexin and chafuroside move to the n-butanol solvent fraction.

More specifically, in the above purification step (HA), allowing the aqueous fraction of liquid-liquid partition to pass through a synthetic adsorbent or the like and to wash with water sufficiently, the adsorption part is eluted with 10-60% methanol (preferably 30% methanol), and is fractioned by gel filtration, silica gel column chromatography or the like. Then, each elution fraction is heated at 140-190° C. for 5-180 minutes (preferably at 160° C. for 40 minutes) and the content of chafuroside produced after heating is determined by LC-MS/MS analysis. Only the fraction having the highest amount of production is subjected to purification by HPLC.

Examples of adsorption chromatography to be used include trade name "Diaion SP825" manufactured by Mitsubishi Chemical Corporation, "Diaion SP207" manufactured by Mitsubishi Chemical Corporation, "Amberlite XAD" manufactured by ORGANO CORPORATION, silica gel for chromatography manufactured by Wako Pure Chemical Industries Ltd. and Merck KGaA, or the like. For gel filtration, gel filtration chromatography such as trade name "Sephadex LH-20" manufactured by Pharmacia and "Bio Gel P-2" can be used.

As a method of LC-MS/MS analysis, a method of HPLC-MS/MS analysis using a methanol aqueous solution or an acetonitrile aqueous solution can be used. Examples of the HPLC-MS/MS analysis include "Cadenza CD C18 HPLC-MS/MS analysis" using a C18 column manufactured by Imtakt Corporation and a specific solvent.

As for the above-mentioned methanol aqueous solution or the acetonitrile aqueous solution, it is more preferable to use a 20-80 wt % methanol aqueous solution or a 10-60 wt % acetonitrile aqueous solution for the reason that it is possible to carry out quantitative determination of chafuroside or the analogues thereof contained in tea leaves and fractions obtained during the process of separation after heating them with high accuracy in HPLC-MS/MS analysis.

(3) Method for Synthesizing Sulfated C-Glycoside from Flavone C-Glycoside

The sulfated C-glycoside of the preset invention can also be obtained by synthesizing from flavone C-glycoside represented by the following general formulas (A0) or (B0). In the following general formula (A0) and (B0), each of $R_1$, $R_2$ and $R_3$ independently represents a hydrogen atom or an OH group.

[Chemical Formula 10]

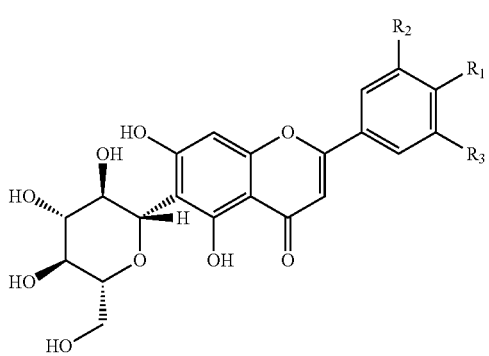

A0

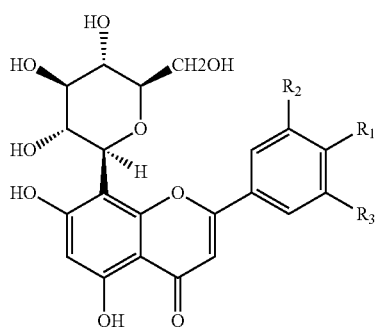

B0

Examples of the flavone C-glycosides represented by the above general formulas (A0) or (B0) include compounds A0-1, A0-2, A0-3, A0-4, B0-1, B0-2, B0-3 and B0-4 represented by the following formulas, wherein $R_1$, $R_2$ and $R_3$ represent synonymously with those in the above general formula (A1) and (B1) respectively.

[Chemical Formula 11]

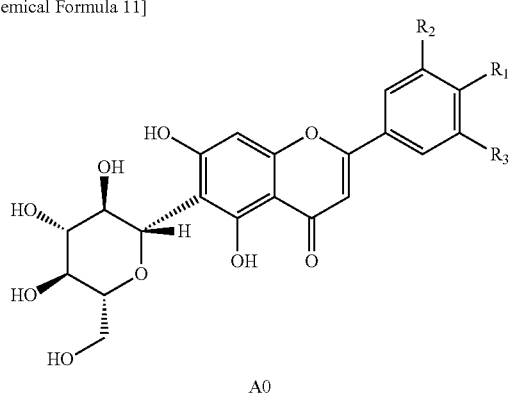

A0

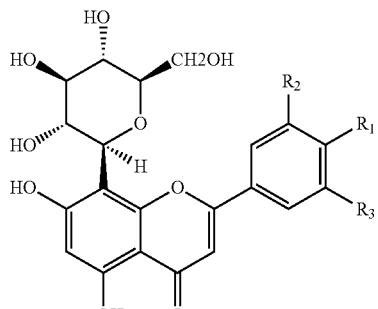

B0

| $R_1$ | $R_2$ | $R_3$ | |
|---|---|---|---|
| H | H | H | A0-1 |
| OH | H | H | A0-2 |
| OH | OH | H | A0-3 |
| OH | OH | OH | A0-4 |
| H | H | H | B0-1 |
| OH | H | H | B0-2 |
| OH | OH | H | B0-3 |
| OH | OH | OH | B0-4 |

A0-2 isovitexin
B0-2 Vitexin

Particularly preferable examples of the compounds represented by the above general formula (A0) include isovitexin which is the above compound (A0-2). Particularly preferable examples of the compounds represented by the above general formula (B0) include vitexin which is the above compound (B0-2).

The method for synthesizing the sulfated C-glycosides of the present invention is characterized in that it comprises a step of reacting a flavone C-glycoside represented by the above general formula (A0) or (B0) with a sulfate group-introducing agent to sulfate said flavone C-glycoside. When synthesizing a precursor of chafuroside A, isovitexin is used as a flavone C-glycoside. When synthesizing a precursor of chafuroside B, vitexin is used as a flavone C-glycoside.

Though the sulfate group-introducing agents should not be limited particularly, examples thereof include a compound selected from the group consisting of a pyridine-SO$_3$ (1:1) complex, sulfur-DCC and a triethylamine-SO$_3$ complex.

Among the above-mentioned synthesizing methods, a method for synthesizing chafuroside precursors A and B from isovitexin and vitexin respectively will be mentioned more specifically below.

In the first stage, OH groups of 4-position and 5-position of isovitexin or vitexin are protected in advance. For introduction of protecting groups, benzaldehyde dimethylacetal-PPTS, benzaldehyde-zinc chloride or the like can be used.

Subsequently, said compound wherein protecting groups are introduced at 4-position and 5-position is reacted with a sulfate group-introducing agent to introduce a sulfate group at intended 2-position. The reaction temperature is preferably 20-80° C.; more preferably 30-40° and the reaction time is 0.5-8 hours, more preferably 2-4 hours.

The 2"- or 3"-sulfated isovitexin or vitexin derivatives wherein 4- and 5-OH groups are protected are subjected to a hydrolysis treatment by a cation exchange resin (IR-120), 40% acetic acid or the like to remove the protection group. Thereafter, the desired chafuroside precursor can be isolated and purified by partition column chromatography using Sep-Pack C18 column, HPLC using ODS-C18 column, gel filtration or the like.

(4) Method for Producing Chafuroside and Chafuroside Analogs

The method for producing chafuroside and chafuroside analogs of the present invention is characterized in that it comprises a step of heating said sulfated C-glycoside at 140-190° C., preferably 150-180° C.

It is assumed that, by heating sulfated C-glycosides, intramolecular cyclization reaction would proceed through a transition state to produce chafuroside and chafuroside analogs. Examples of the chemical reactions of production of chafuroside A from chafuroside precursor A (isovitexin 2″-sulfate) and production of chafuroside B from chafuroside precursor B (vitexin 2″-sulfate) are shown as chemical reaction formulas below:

[Chemical Formula 12]

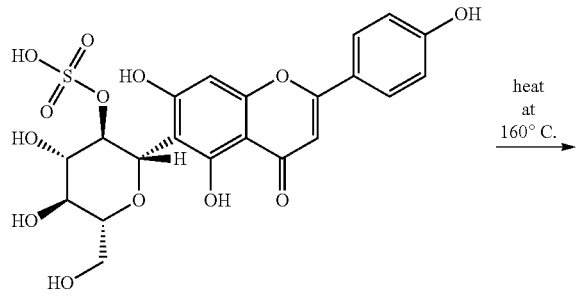

Isovitexin 2″-sulfate heat at 160° C.

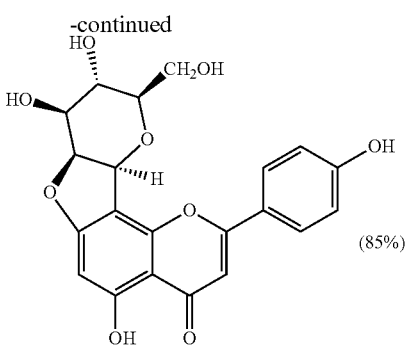

Chafuroside A

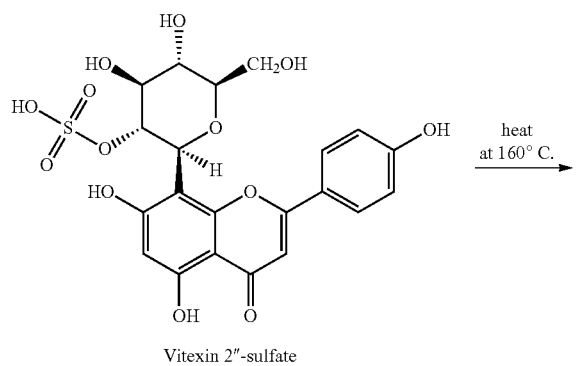

Vitexin 2″-sulfate heat at 160° C.

Chafuroside B (85%)

Among the above-described sulfate C-glycosides, the sulfate C-glycoside represented by the general formula (A1) gives chafuroside and chafuroside analogs represented by the following general formula (A2). The sulfate C-glycoside represented by the general formula (B1) gives chafuroside and chafuroside analogs represented by the following general formula (B2). In the following general formula (A2) and (B2), $R_1$, $R_2$ and $R_3$ represent synonymously with those in the above general formula (A1) and (B1) respectively.

[Chemical Formula 13]

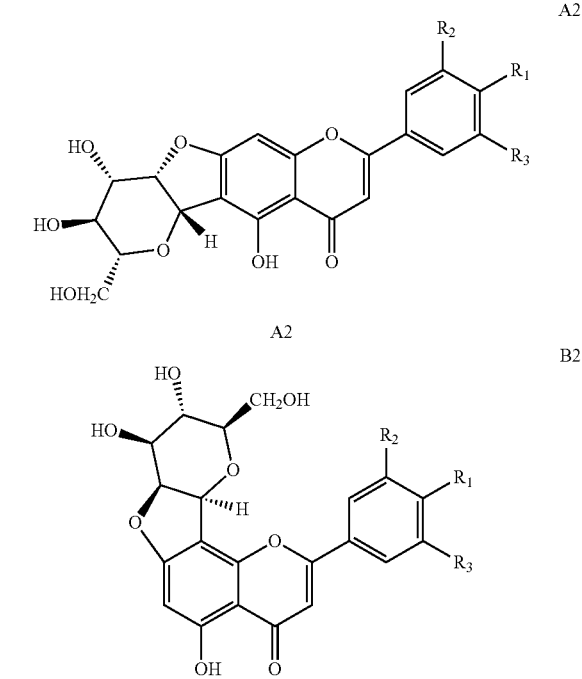

More specifically, among the above-described sulfate C-glycosides, sulfate C-glycosides represented by the following general formulas (A1-1) and (B1-1) give chafuroside analogs represented by the following general formulas (A2-1) and (B2-1) respectively. Chafuroside precursors A and B represented by the following general formulas (A1-2) and (B1-2) give chafurosides A and B represented by the following general formulas (A2-2) and (B2-2) respectively. Sulfate C-glycosides represented by the following general formulas (A1-3) and (B1-3) give chafuroside analogs represented by the following general formulas (A2-3) and (B2-3) respectively. Sulfate C-glycosides represented by the following general formulas (A1-4) and (B1-4) give chafuroside analogs represented by the following general formulas (A2-4) and (B2-4) respectively.

[Chemical Formula 14]

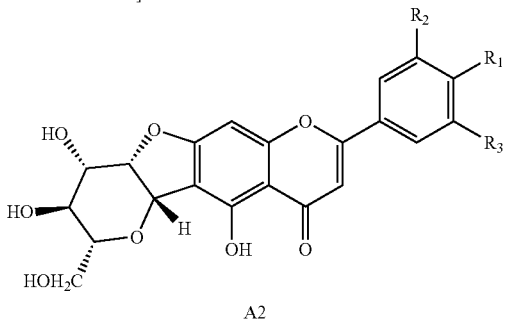

A2

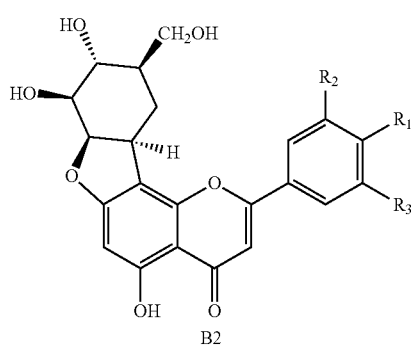

B2

| $R_1$ | $R_2$ | $R_3$ | |
|---|---|---|---|
| H | H | H | A2-1 |
| OH | H | H | A2-2 |
| OH | OH | H | A2-3 |
| OH | OH | OH | A2-4 |
| H | H | H | B2-1 |
| OH | H | H | B2-2 |
| OH | OH | H | B2-3 |
| OH | OH | OH | B2-4 |

EXAMPLES

The present invention will be described in more detail below referring to Examples. Note that the scope of the present invention is not limited by the following examples.

Example 1

In Example 1, contents of chafuroside A and chafuroside B contained in various types of tea leaves were analyzed by the following process. Firstly, chafurosides A and B were synthesized, by means of Mitsunobu reaction, from isovitexin and vitexin respectively which had been prepared using Puriri (Vitex lucens) of New Zealand origin as a source. A standard curve for analyzing chafurosides was created using them, and quantitative analyses of chafurosides A and B in various types of tea leaves were performed on the basis thereof.

(1) Reagents

All the reagents and solvents used for synthesizing were special grade products manufactured by Wako Pure Chemical Industries Ltd. As for a partition-type separating agent, trade name "ODS C18" filled in "Sep-Pack C18 Cartridge" manufactured by Waters Corp. Trade name "Sephadex LH-20" manufactured by Pharmacia was used for gel filtration. Trade name "Diaion SP825" manufactured by Mitsubishi Chemical Corporation was used as an adsorption separating agent. Trade name "Cadenza CD-C18" manufactured by Imtakt Corporation was used as a HPLC column for separation.

(2) Samples

Following species were used as tea leaves for experimental use.

Green Tea: Shizu 7132, Yabukita, Sayamakaori
Houji Tea: Shizu 7132, Yabukita
Oolong Tea: Shizu 7132, Suisen, Tetsukannon
Black Tea: Shizu 7132, Assam, Darjeeling Note that green tea, oolong tea and black tea leaves from Shizu 7132 were prepared by a specialist on tea processing resident of Shimada-shi, Shizuoka-ken.

After grinding tea leaves by a coffee mill, 0.2 g of the ground product was extracted with 2 ml of 50% MeOH under stirring for 20 minutes at 90° C. The extraction was repeated twice. The extraction liquid was concentrated, dried and solidified under reduced pressure, and was then dissolved in 1 ml of $H_2O$. Subsequently, it was extracted with n-BuOH (1 ml×2), and the n-BuOH fraction thus obtained was concentrated, dried and solidified under reduced pressure. Then, it was dissolved in 0.5 ml of 30%-$CH_3CN$ to obtain a sample for analysis.

(3) Methods for Measurement and Analysis

NMR measurements were performed using trade name "JNM-ECA 500" manufactured by JEOL. LC-MS/MS analyses were performed using trade names "Agilent 1100" and "API 2000", manufactured by Applied Biosystems in combination. QTOF-MS measurements were performed using trade name "QSTAR" manufactured by Applied Biosystems. UV measurements were performed using trade name "U3900", manufactured by Hitachi, Ltd. Heat treatment was conducted using a heating thermostat bath for micro-distillation manufactured by Buchi.

(4) Analysis of Chafurosides A and B, Isovitexin, and Vitexin

Reference standard solutions of 0.2 ng/ml, 1.0 ng/ml, 10 ng/ml, 100 ng/ml, and 1000 ng/ml were prepared from chafurosides A and B, isovitexin, and vitexin which had been synthesized preliminary. Gradient elution was carried out by changing 15-50% for 20 minutes using these reference standard solutions, using trade name "Cadenza CD-C18" (3×150 mm) as a column and using a $H_2O$—$CH_3CN$ mixed solvent for elution development.

A calibration curve was prepared from the peak area of chromatogram of each compound obtained using 10 μl of the reference standard solution of each concentration. On the basis of the calibration curve, LC-MS/MS quantitative determination using ESI was performed. Conditions for MS/MS were shown below.

TABLE 1

| ESI Setting Parameters of Chafuroside A and B, Vitexin and Isovitexin | | | | |
|---|---|---|---|---|
| Compound | chafuroside A | chafuroside B | vitexin | isovitexin |
| Precursor/product m/z, ion and polarity | 413.0([M − H]$^-$)/293.0 | 413.2([M − H]$^-$)/292.8 | 431.2([M − H]$^-$)/311.0 | 431.0([M − H]$^-$)/311.2 |

TABLE 1-continued

ESI Setting Parameters of Chafuroside A and B, Vitexin and Isovitexin

| Compound | chafuroside A | chafuroside B | vitexin | isovitexin |
|---|---|---|---|---|
| Collision energy(eV) | 36 | 36 | 32 | 32 |
| Capillary voltage (kV) | 4 | 4 | 4 | 4 |
| Temperature (□) | 500 | 500 | 500 | 500 |

(5) Results and Discussion

The results of analyzing the contents of Chafuroside A, chafuroside B, isovitexin and vitexin contained in tea leaves of each brand mentioned above are shown in the following Table 2. The unit of the contents shown in said table is "ng/g".

TABLE 2

Contents of Chafuroside A in Commercial Tealeaves

| | chafuroside A | chafuroside B | vitexin | isovitexin |
|---|---|---|---|---|
| green tea Shizu 7132 | 51.6 ± 4.0 | 41.9 ± 6.7 | 102114.7 ± 2036.1 | 88394.5 ± 6935.7 |
| green tea Yabukita | 37.8 ± 0.2 | 23.5 ± 0.5 | 96440.7 ± 18935.6 | 89432.7 ± 18769.9 |
| green tea Sayamakaori | 34.0 ± 0.8 | 23.9 ± 1.3 | 48026.3 ± 1248.2 | 41567.5 ± 176.7 |
| houji tea Shizu 7132 | 4980.4 ± 168.0 | 3649.5 ± 349.3 | 57064.0 ± 34272.0 | 64472.4 ± 36660.2 |
| houji tea Yabukita-1 | 1977.3 ± 147.1 | 2067.0 ± 102.1 | 64522.4 ± 813.9 | 60946.1 ± 488.6 |
| houji tea Yabukita-2 | 3143.5 ± 344.3 | 2988.4 ± 302.1 | 44535.4 ± 414.8 | 5143.5 ± 4436.3 |
| oolong tea Shizu 7132 | 50.4 ± 0.3 | 38.7 ± 1.9 | 56697.0 ± 1206.0 | 52623.9 ± 286.4 |
| oolong tea Suisen | 8575.2 ± 764.1 | 7957.8 ± 362.2 | 32342.4 ± 1977.4 | 28793.6 ± 710.2 |
| oolong tea Tekkannnon | 1693.7 ± 173.9 | 1143.3 ± 159.1 | 41754.9 ± 2696.7 | 40207.5 ± 2597.7 |
| black tea Shizu 7132 | 78.2 ± 1.9 | 53.1 ± 2.3 | 55584.1 ± 2889.9 | 49888.0 ± 2255.1 |
| black tea Assam | 18.2 ± 1.9 | 23.1 ± 2.3 | 22584.1 ± 2889.9 | 19888.0 ± 2255.1 |
| black tea Darjeeling | 97.6 ± 39.5 | 72.5 ± 9.2 | 20640 ± 2410.0 | 19002.9 ± 2204.1 | n = 3, mean ± S.E.

In all the tea leaves of the above-mentioned brands, chafuroside A and chafuroside B were detected together with isovitexin and vitexin. The contents of isovitexin and vitexin were from several dozen to 100 μg. From the viewpoint of mean values, the contents were shown high in the order of green tea, houji tea, oolong tea and black tea. There was no large difference among tea species and brands.

Meanwhile, a large difference among tea leaves was recognized for chafurosides A and B. The contents in green tea and black tea were several dozen ng per gram of tea leaves, and there was little difference among the brands. Compared to them, the contents thereof in houji tea and oolong tea, except for that produced from Shizu 7132, were several dozen μg per gram of tea leaves though the values somewhat vary, which were remarkably higher than the contents in green tea and black tea. There was no significant difference among the brands for houji tea, whereas there was a large difference for oolong tea.

Green tea leaves were prepared by steaming fresh young tea leaves, then cooling quickly, followed by drying with rolling by hand with heating at around 80° C. to evaporate water. Black tea leaves were processed by softening young tea leaves for around 8 hours, drying water and then conducting oxidative fermentation for several hours with rolling by hand, followed by rapid drying with hot air at around 90° C. Oolong tea leaves were prepared from fully grown tea leaves by softening under sunlight for a few hours, followed by semi-fermentation with shaking on a bamboo tray in a room, then neutralizing the enzyme with hot air at 160-260° C. for a short time, and finally drying at around 90° C. Houji tea leaves were prepared from green tea leaves by roasting at 160-200° C. for a short time.

Tea leaves having a large content among oolong tea species at room temperature showed signs of roasting by strongly firing, whereas oolong tea leaves prepared from Shizu 7132 showed no signs thereof. In addition, green tea leaves prepared from the same tea leaves of same species were drastically increased in the contents after roasting.

From the above results, it was assumed that one of the factors for producing chafuroside A and chafuroside B would be heating at high temperature of 160° C. or higher.

No correlated relationship was shown between the contents of chafurosides A and B and the contents of isovitexin and vitexin in tea leaves of various brands.

(6) Optimization of Factors for Production

Oolong tea leaves prepared from Shizu 7132 were heated for 40 minutes at 120, 140, 160, 180 and 200° C., and then the contents of chafurosides A and B in the tea leaves were determined respectively to obtain the results shown in Table 3. Unit of contents shown in Table 3 is "ng/g".

TABLE 3

Contents of Chafuroside A and B in Leaves of Oolong tea prepared from Shizu 7132 after Heating

| Temperature (° C.) | 140 | 160 | 180 | 200 |
|---|---|---|---|---|
| chafuroside A | 280.4 ± 16.0 | 8649.5 ± 249.3 | 7764.0 ± 272.0 | 72.4 ± 10.2 |
| chafuroside B | 256.3 ± 14.3 | 7259.2 ± 203.5 | 7436.8 ± 254.7 | 68.9 ± 8.8 | n = 3, mean ± S.E.

In addition, after heating for 20 40 60 and 80 minutes at heating temperature of 160° C., the contents of chafurosides A and B in the tea leaves were determined respectively to obtain the results shown in Table 4. Unit of contents shown in Table 4 is "ng/g".

TABLE 4

Contents of Chafuroside A and B in Leaves of Oolong tea prepared from Shizu 7132 after Heating at 160° C.

| Time (min) | 20 | 40 | 60 | 80 |
|---|---|---|---|---|
| chafuroside A | 3480.4 ± 216.0 | 7658.5 ± 449.3 | 8794.0 ± 272.0 | 8872.4 ± 310.2 |
| chafuroside B | 3244.7 ± 224.5 | 6954.4 ± 409.7 | 7577.5 ± 244.3 | 7994.5 ± 298.9 | n = 3, mean ± S.E.

As shown in the above results, it made clear that chafurosides A and B in processed tea leaves were produced on heating and the optimum temperature was in the range of 160-180° C. for fully grown tea leaves. It was shown that it would be decomposed when the temperature was too high. The production amount became a local maximum value after about 40 minutes of heating at 160° C., and it was substantially constant and did not increase when heating was prolonged even further.

When heating green tea, oolong tea and black tea leaves of each brand at optimum temperature for optimum time, the contents of chafurosides A and B from green tea, oolong tea and particular black tea leaves drastically increased to be 15 μg/g (tea leaves) on average. However, the content thereof in commercially available common black tea was, though being drastically increased, only a few μg/g (tea leaves) on average. Thus, it was shown that oxidative fermentation in tea processing was also important for the production of chafurosides A and B.

Example 2

In this example, isolation, purification and structural determination of chafuroside precursors were carried out. As mentioned above, chafurosides A and B can be produced by Mitsunobu reaction wherein triphenylphosphine and diethyl azodicarboxylate are reacted with isovitexin and vitexin. Therefore, the following studies were firstly carried out about extraction of the precursors and its properties.

(1) Isolation and Purification of Chafuroside Precursors 1 g of oolong tea leaves prepared from Shizu 7132 was ground and was subjected to extract with MeOH, 50%-MeOH and water (1 ml) under reflux. After concentrating, drying and solidifying the extract liquid under reduced pressure, it was suspended in water (0.4 ml) and then was extracted with n-BuOH (4 ml and 1 ml). All of the extracts, their aqueous fractions and n-BuOH fractions obtained by liquid-liquid partition thereof were heated at 160° C. for 40 minutes.

In the result, the production of chafurosides A and B by heating was detected only in all of the extracts and their aqueous fractions. Isovitexin and vitexin move to n-BuOH fractions in the case of liquid-liquid partition with water and n-BuOH. These results indicated that, unlike with isovitexin and vitexin, the precursors of chafurosides A and B were highly-polar substance having higher water solubility than them.

On the basis of the above results, isolation of the precursors was carried out by a method wherein, after drying and solidifying the fraction obtained by each step of partition and then heating at 160° C. for 40 minutes, chafurosides A and B were subjected to LC-MS/MS analyses and only the fraction having the highest production amount of chafurosides A and B was subjected to the next isolation. One example of isolation procedures of the precursors thus established was shown in FIG. 1 (a chart diagram).

1 kg of oolong tea leaves prepared from Shizu 7132 was ground and subjected to extract with MeOH (10 L) under reflux. The extract liquid thus obtained was concentrated, dried and solidified under reduced pressure. The extract thus obtained (348 g) was suspended in water (3 L) and was extracted with n-BuOH (4 L and 1 L). The aqueous fraction (142 g) was dissolved in water (3 L) and applied in "Diaion SP825" (2.4 L), then after washing with water (3 L), it was eluted with 30%-methanol (8 L). The 30%-methanol fraction eluted (248 g) was fractioned with gel filtration on "Sephadex LH-20" (12 L) using MeOH for development.

Fraction eluted between Kd=2.1 and 2.8 (1.97 g) was subjected to a column chromatography on "ODS-C18" (400 mL) using 20%-acetonitril solution for development to obtain crude fractions containing precursors of chafurosides A and B (87 mg and 63 mg, respectively).

Finally, the fractions were purified on HPLC using "Cadenza CD-C18" column and 0.05% $HCO_2H$—$CH_3CN$ (82:18) to obtain chafuroside precursor A (prechafuroside A) and prechafuroside B (5 mg and 4 mg, respectively).

As mentioned above, according to the present invention, purification can be carried out by subjecting the aqueous fraction to a strongly basic ion-exchange resin and purifying the adsorption part by means of gel filtration using "Sephadex LH-20" (12 L), "ODS-C18" (400 mL) column chromatography using 20%-acetonitril solution for developing, HPLC using "Cadenza CD-C18" column and 0.05% $HCO_2H$—$CH_3CN$ (82:18) or the like.

(2) Structural Determination of Chafuroside Precursors

From the precise molecular weights of prechafurosides A and B obtained by negative mode QTOF-MS analyses (prechafuroside A: m/z 511.05612 (M—H)$^-$ and prechafuroside B:m/z 511.05643 (M—H)$^-$) and $^{13}$C-NMR data (see the following Table 5), the molecular formulas of prechafurosides A and B were determined as "$C_{21}H_{20}O_{13}S$" (calcd. for $C_{21}H_{20}O_{13}S$—H, 511.05625).

On UV spectra, prechafuroside A had wavelengths of maximum absorption at 330 nm (ε 40200) and 284 nm (ε 64200) same as those of isovitexin, and prechafuroside B had wavelengths of maximum absorption at 325 nm (ε 44100) and 285 nm (ε 62200) same as those of vitexin. In addition, isovitexin was produced from prechafuroside A and vitexin was produced from prechafuroside B almost quantitatively on solvolysis with pyridine-dioxane (1:1).

As is clear from $^{13}$C-NMR data of prechafurosides A and B, isovitexin and vitexin shown in Table 5, there were no significant differences in the chemical shifts of carbon atoms between prechafuroside A and isovitexin and between prechafuroside B and vitexin, except for C-2".

Differences of chemical shifts of the C-2" carbons between prechafuroside A and isovitexin and between prechafuroside B and vitexin and low magnetic shifts thereof strongly indicated that prechafuroside A and prechafuroside B were the compounds wherein OH groups at C-2" positions of isovitexin and vitexin were sulfated respectively.

TABLE 5

表5 ($^{13}$C-NMR data for prechafuroside A, isovitexin, prechafuroside B and vitexin in DMSO-$d_6$ (ppm))

| No. | isovitexin $\delta_C$ | prechafuroside A $\delta_C$ | vitexin $\delta_C$ | prechafuroside B $\delta_C$ |
|---|---|---|---|---|
| 1 | | | | |
| 2 | 164.9 | 163.8 | 162.4 | 162.7 |
| 3 | 104.0 | 104.7 | 102.4 | 102.9 |
| 4 | 184.1 | 182.8 | 182.0 | 182.7 |
| 5 | 158.8 | 156.6 | 155.9 | 157.0 |
| 6 | 109.2 | 109.4 | 98.1 | 98.4 |
| 7 | 166.2 | 164.9 | 163.9 | 164.3 |
| 8 | 95.4 | 94.5 | 104.0 | 103.8 |
| 8a | 162.0 | 161.9 | 160.3 | 161.0 |
| 4a | 105.3 | 103.4 | 104.5 | 104.5 |
| 1' | 123.2 | 121.7 | 121.5 | 122.3 |
| 2' | 129.4 | 129.1 | 128.8 | 129.4 |
| 3' | 117.1 | 116.5 | 115.7 | 116.3 |
| 4' | 162.8 | 161.8 | 161.0 | 161.6 |
| 5' | 117.1 | 116.5 | 115.7 | 116.3 |
| 6' | 129.4 | 129.1 | 128.8 | 129.4 |
| 1" | 75.3 | 70.2 | 73.3 | 71.1 |
| 2" | 72.9 | 76.0 | 70.8 | 76.5 |
| 3" | 80.0 | 78.7 | 78.6 | 78.6 |
| 4" | 71.6 | 70.7 | 70.5 | 71.4 |
| 5" | 82.7 | 81.5 | 81.7 | 81.9 |
| 6" | 62.4 | 62.1 | 61.3 | 61.5 |

Assignments were based on $^1$H-$^1$H-COSY, $^1$H-$^{13}$C-COSY and HMBC experiments.

On the basis of the above results, structures of prechafurosides A and B were concluded to be "isovitexin 2"-O-sulfate" and "vitexin 2"-O-sulfate" represented by the following chemical formulas respectively. In the following chemical formulas, "isovitexin 2"-O-sulfate" is shown at the left and "vitexin 2"-O-sulfate" is shown at the right.

[Chemical Formula 15]

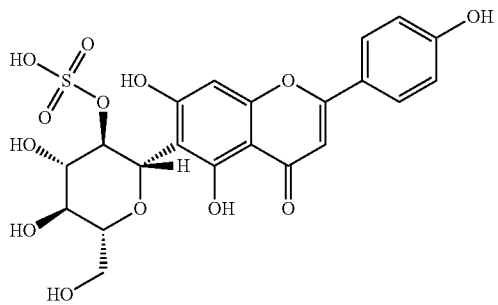
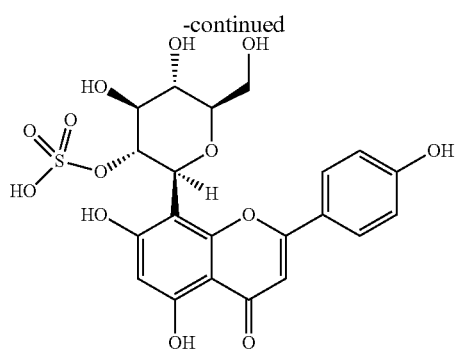

The proposed structures were well supported by QTOF-MS/MS measurements wherein prechafuroside A gave fragment ions attributed to $C_{21}H_{19}O_{10}$ corresponding to [isovitexin-H] (m/z 431.1040 (calcd. for $C_{21}H_{19}O_{10}$, 431.0978)) and fragment ions corresponding to $OSO_3H$ (m/z 96.9618 (calcd. for $HSO_4$, 96.9601)), and prechafuroside B also gave fragment ions attributed to $C_{21}H_{19}O_{10}$ corresponding to [vitexin-H] (m/z 431.1040 (calcd. for $C_{21}H_{19}O_{10}$, 431.0978)) and fragment ions corresponding to $OSO_3H$ (m/z 96.9604 (calcd. for $HSO_4$, 96.9601)) (see the following chemical formulas). Moreover, since the physicochemical data between the presumed compounds obtained by synthesis described below and prechafurosides obtained from oolong tea leaves completely coincided, these structures were determined as isovitexin 2"-O-sulfate and vitexin 2"-O-sulfate respectively.

FIGURE Fragmentation of Prechafuroside A and B

[Chemical Formula 16]

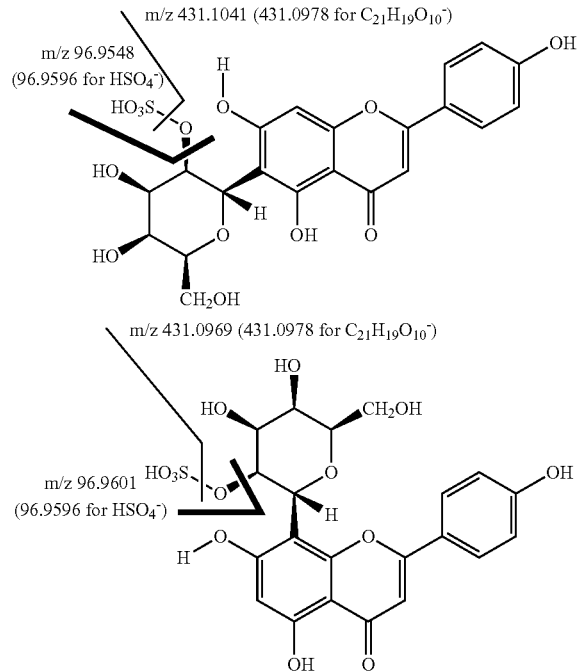

It is known that, in the case of sulfated saccharides and bile alcohols wherein the hydroxy groups of side chains are sulfated, adjacent OH groups become $O^-$ and a nucleophilic reagent by strong alkaline treatment, and as a result, $S_N2$ type substitution reaction is induced to proceed intramolecular cyclization reaction.

In the case of prechafurosides A and B, if intermolecular cyclization reactions proceed via a transition state shown in the following chemical formulas on heating to produce chafuroside A and chafuroside B respectively, conversion of prechafurosides A and B into chafurosides A and B on heating can well be interpreted.

Formation mechanism of chafuroside A and B from prechafuroside A and B

[Chemical Formula 17]

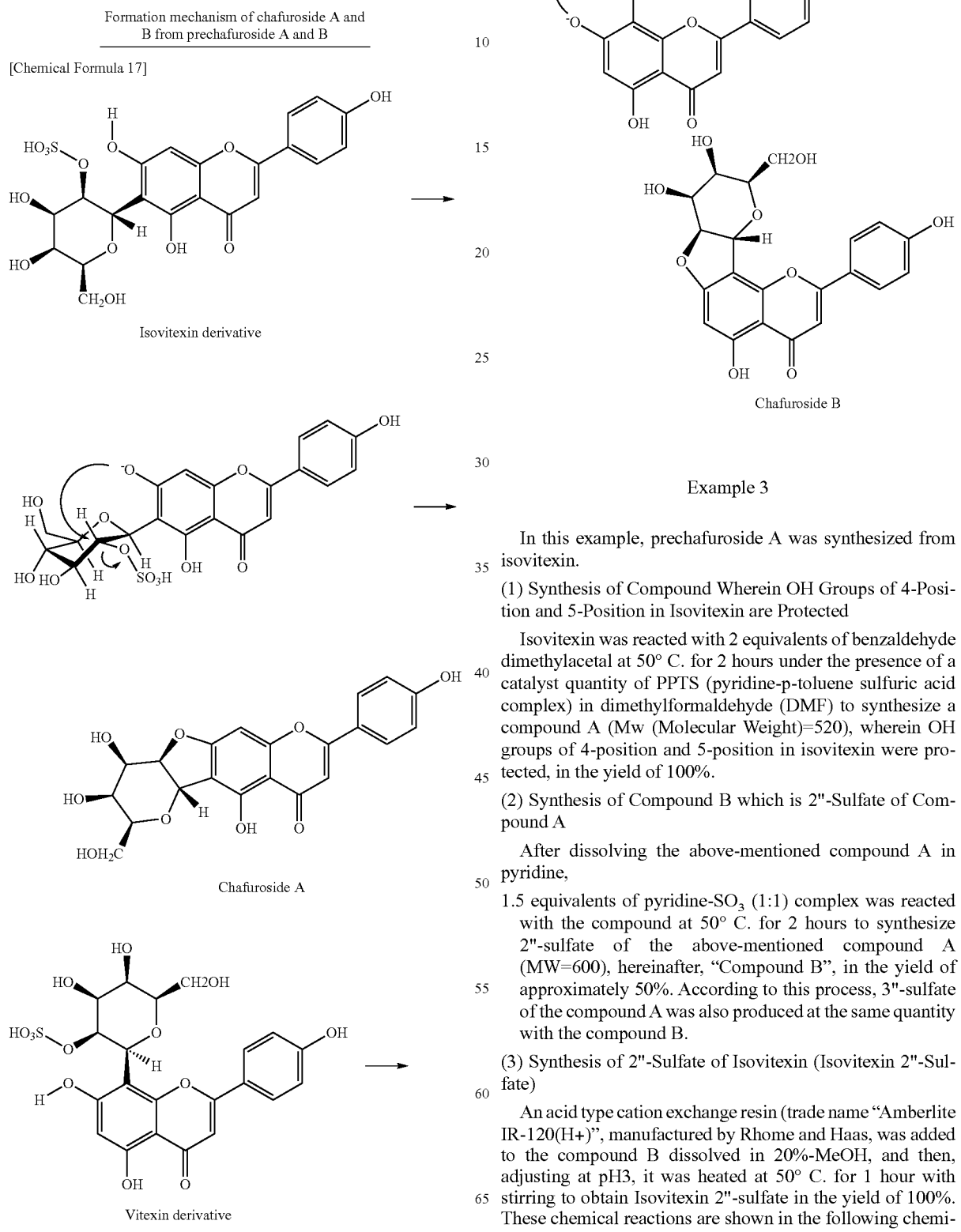

Chafuroside B

Example 3

In this example, prechafuroside A was synthesized from isovitexin.

(1) Synthesis of Compound Wherein OH Groups of 4-Position and 5-Position in Isovitexin are Protected Isovitexin was reacted with 2 equivalents of benzaldehyde dimethylacetal at 50° C. for 2 hours under the presence of a catalyst quantity of PPTS (pyridine-p-toluene sulfuric acid complex) in dimethylformaldehyde (DMF) to synthesize a compound A (Mw (Molecular Weight)=520), wherein OH groups of 4-position and 5-position in isovitexin were protected, in the yield of 100%.

(2) Synthesis of Compound B which is 2"-Sulfate of Compound A

After dissolving the above-mentioned compound A in pyridine, 1.5 equivalents of pyridine-$SO_3$ (1:1) complex was reacted with the compound at 50° C. for 2 hours to synthesize 2"-sulfate of the above-mentioned compound A (MW=600), hereinafter, "Compound B", in the yield of approximately 50%. According to this process, 3"-sulfate of the compound A was also produced at the same quantity with the compound B.

(3) Synthesis of 2"-Sulfate of Isovitexin (Isovitexin 2"-Sulfate)

An acid type cation exchange resin (trade name "Amberlite IR-120(H+)", manufactured by Rhome and Haas, was added to the compound B dissolved in 20%-MeOH, and then, adjusting at pH3, it was heated at 50° C. for 1 hour with stirring to obtain Isovitexin 2"-sulfate in the yield of 100%. These chemical reactions are shown in the following chemical formulas.

[Chemical Formula 18]
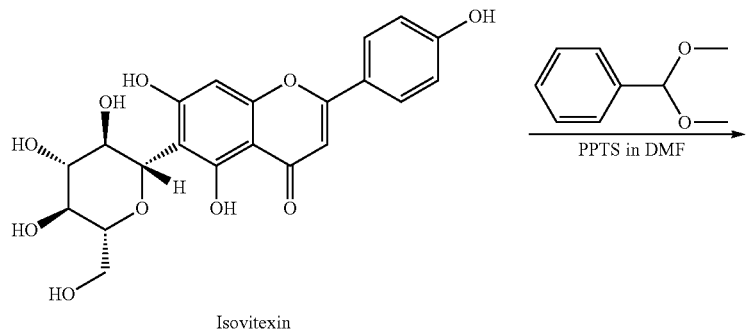
Isovitexin
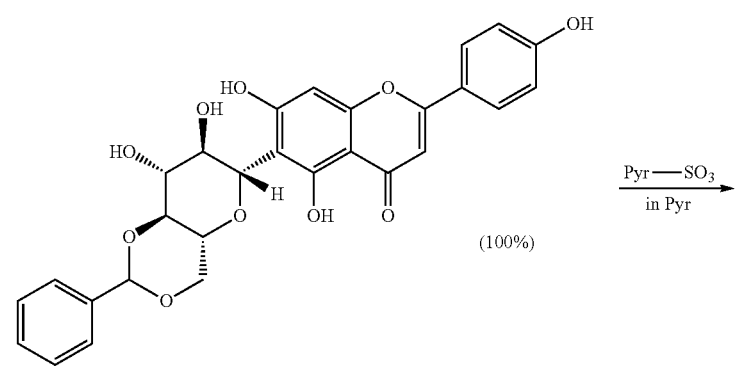
(100%)
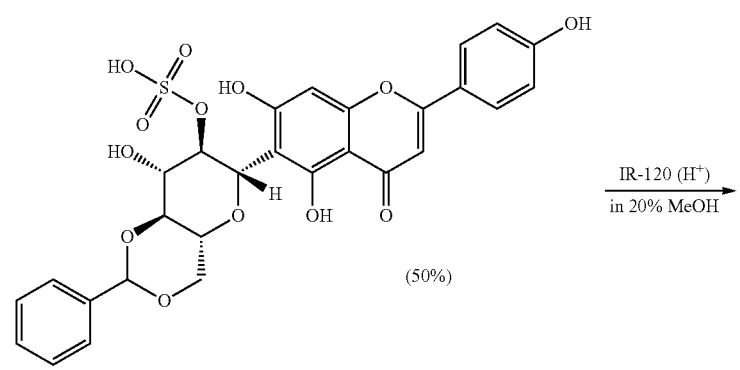
(50%)
(100%)
Isovitexin 2″-sulfate (4) The structure of Isovitexin 2"-sulfate thus obtained was compared directly with that of the compound extracted from tea leaves in the above Example 2, and it was confirmed that Isovitexin 2"-sulfate was the above-mentioned prechafuroside A. When heating said Isovitexin 2"-sulfate at around 160-170° C., chafuroside A was produced in the yield of 85%.

Example 4

Prechafuroside B was synthesized from vitexin in this Example.

(1) Synthesis of Compound Wherein OH Groups of 4-Position and 5-Position in Vitexin are Protected Vitexin was reacted with 2 equivalents of benzaldehyde dimethylacetal at 50° C. for 2 hours under the presence of a catalyst quantity of PPTS (pyridine-p-toluene sulfuric acid complex) in dimethylformaldehyde (DMF) to synthesize a compound C (Mw (Molecular Weight)=520), wherein OH groups of 4-position and 5-position in vitexin were protected, in the yield of 100%.

(2) Synthesis of Compound D which is 2"-Sulfate of Compound C

After dissolving the above-mentioned compound C in pyridine, 1.5 equivalents of pyridine-$SO_3$ (1:1) complex was reacted with the compound at 50° C. for 2 hours to synthesize 2"-sulfate of the above-mentioned compound C (MW=600), hereinafter, "Compound D", in the yield of approximately 50%. According to this process, 3"-sulfate of the compound C was also produced at the same quantity with the compound D.

(3) Synthesis of 2"-Sulfate of Vitexin (Vitexin 2"-Sulfate)

An acid type cation exchange resin (trade name "Amberlite IR-120(H+)", manufactured by Rhome and Haas, was added to the compound D dissolved in 20%-MeOH, and then, adjusting at pH3, it was heated at 50° C. for 1 hour with stirring to obtain Vitexin 2"-sulfate in the yield of 100%. These chemical reactions are shown in the following chemical formulas.

[Chemical Formula 19]

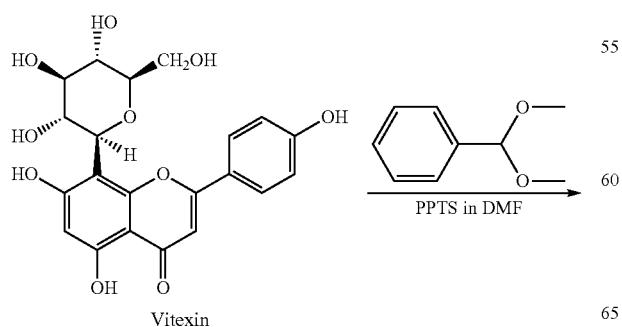

Vitexin

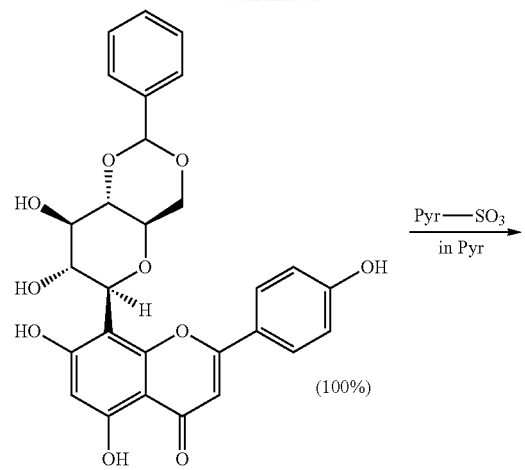

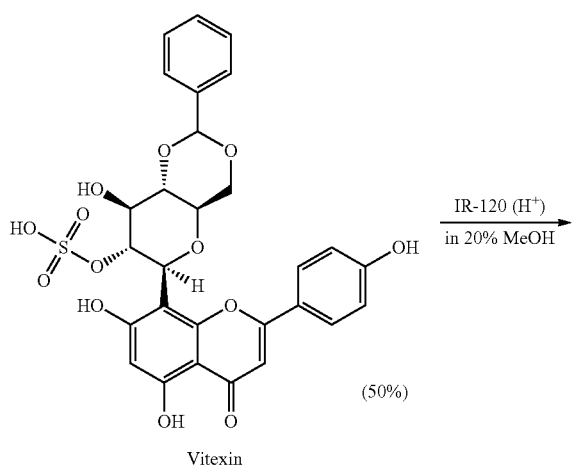

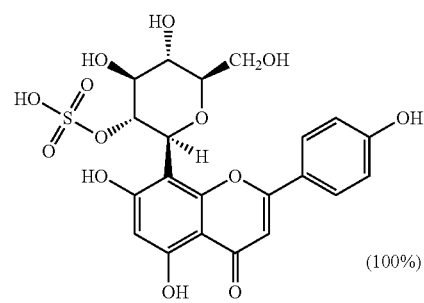

Vitexin 2"-sulfate (4) The structure of Vitexin 2"-sulfate thus obtained was compared directly with that of the compound extracted from tea leaves in the above Example 2, and it was confirmed that Vitexin 2"-sulfate was the above-mentioned prechafuroside B. When heating said Vitexin 2"-sulfate at around 160-170° C., chafuroside B was produced in the yield of 85%.

INDUSTRIAL APPLICABILITY

Chafuroside precursors which are novel compounds found by the present invention (prechafurosides. A and B) is expected to exhibit excellent pharmacological effects in themselves such as an antioxidant effect, an antiallergic effect, an anti-inflammatory effect, an carcinoma inhibition effect and the like. Moreover, it is excellent in affinity for a human body having a high water solubility caused by introduction of sulfate groups. Furthermore, using said prechafurosides, it will be possible to produce chafurosides A and B which are already known to have the above-mentioned medical properties in an extremely high yield.

Thus, according to the present invention, since it is possible to produce chafurosides with a high yield using inexpensive and safe starting materials and reagents though under relatively moderate reaction conditions, industrial mass production is feasible by a scale-up, and it is greatly useful on industry.

The invention claimed is:

1. A sulfated C-glucoside represented by the following general formula (A1) or (B1):

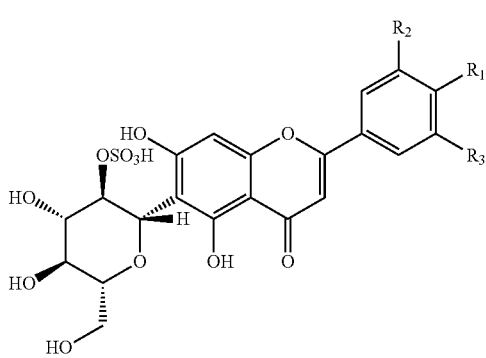

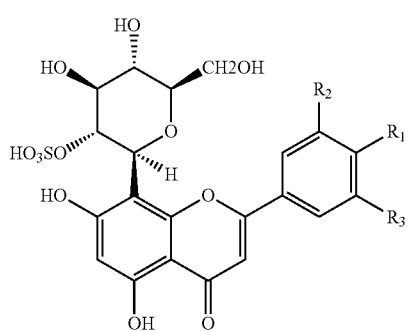

in the above general formula (A1) and (B1), each of $R_1$, $R_2$, and $R_3$ independently represents a hydrogen atom or an OH group.

2. The sulfated C-glycoside according to claim 1 wherein said sulfated C-glycoside is a sulfated derivative of isovitexin represented by the following formula (A1-2) or a sulfated derivative of vitexin represented by the following formula (B1-2):

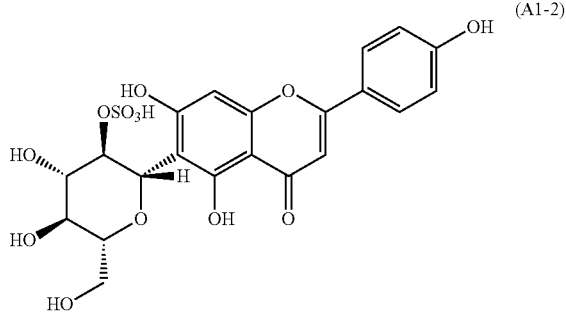

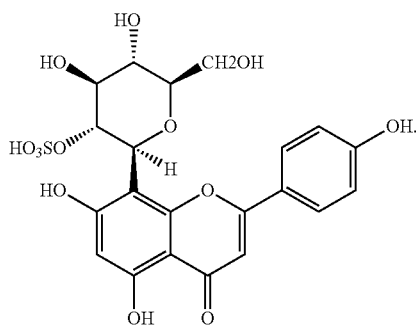

3. A method for isolating a sulfated C-glycoside according to claim 1 or 2, which comprises a step of extracting said sulfated C-glycoside from tea leaves or tea tannins containing said sulfated C-glycoside using water, a lower alcohol solvent having 1 to 3 carbon atoms or a liquid mixture comprising the same.

4. A method for isolating a sulfated C-glycoside according to claim 3, wherein the method comprises the following steps (IE), (RO) and (HA):

(IE) an extraction step wherein a ground product of tea leaves or tea tannins containing said sulfated C-glycoside is extracted with water, a lower alcohol solvent having 1 to 3 carbon atoms or a liquid mixture comprising the same to obtain an extraction liquid containing said sulfated C-glycoside, (RO) a concentration and dry-solidification step wherein said extraction liquid obtained by the above extraction step (IE) is concentrated, dried and solidified by heating under reduced pressure to obtain a dry solid substance containing said sulfated C-glycoside, and (HA) a purification step wherein said dry solid substance containing sulfated C-glycoside obtained by the above concentration and dry-solidification step (RO) is subjected to liquid-liquid partition using water and n-butanol solvent, and then the aqueous fraction is purified by a chemical separation purification method.

5. A method for synthesizing sulfated C-glycoside according to claims 1 or 2, which comprises a step of reacting flavone C-glycoside represented by the following general formulas (AO) or (BO) with a sulfate group-introducing agent to sulfate said flavone C-glycoside:

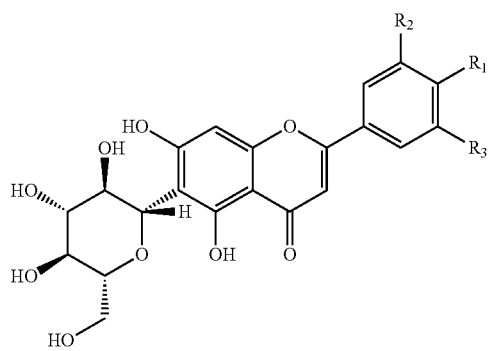

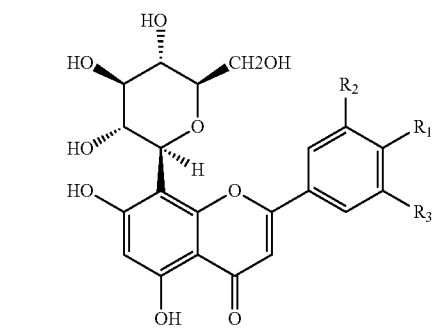

in the above general formula (AO) and (BO), each of $R_1$, $R_2$ and $R_3$ independently represents a hydrogen atom or an OH group.

6. The method for synthesizing sulfated C-glycoside according to claim 5, wherein said sulfate group-introducing agent is selected from the group consisting of pyridine-$SO_3$ complex, sulfur-DCC and triethylamine-$SO_3$ complex.

7. A method for producing chafuroside and chafuroside analogs represented by the following formulas (A2) or (B2), which comprises a step of heating sulfated C-glycoside according to claim 1 or 2 at the temperature of 130-190° C.:

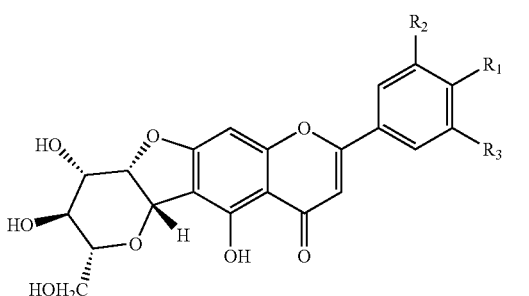

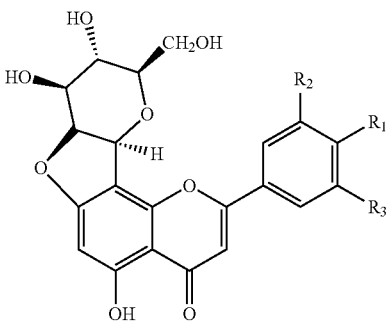

in the above general formula (A2) and (B2), each of $R_1$, $R_2$ and $R_3$ independently represents a hydrogen atom or an OH group.

* * * * *